United States Patent [19]

Laughlin et al.

[11] Patent Number: 5,760,056
[45] Date of Patent: Jun. 2, 1998

[54] PHARMACEUTICAL FORMULATION

[75] Inventors: Sharon M. Laughlin, Phoenixville; Nancy M. Franson, Collegeville, both of Pa.

[73] Assignee: Sanofi Pharmaceuticals, Inc., New York, N.Y.

[21] Appl. No.: 808,761

[22] Filed: Mar. 3, 1997

[51] Int. Cl.$^6$ ............................................. A61K 31/47
[52] U.S. Cl. ............................................. 514/314
[58] Field of Search ............................................. 514/314

[56]  References Cited

U.S. PATENT DOCUMENTS

| | | | |
|---|---|---|---|
| 5,360,615 | 11/1994 | Yu et al. | 424/455 |
| 5,420,141 | 5/1995 | Boigegrain et al. | 514/314 |

FOREIGN PATENT DOCUMENTS

WO88/02625  4/1988  WIPO .

OTHER PUBLICATIONS

Sirenius et al., *J. Pharm. Sci.*, 66, No. 6, Jun. 1979.
Sheen et al., *J. Pharm. Sci.*, 118, No. 2, 1995.

*Primary Examiner*—Raymond Henley, III
*Attorney, Agent, or Firm*—Michael D. Alexander; Mary P. Bauman; Paul E. Dupont

[57]  ABSTRACT

A pharmaceutical formulation comprising

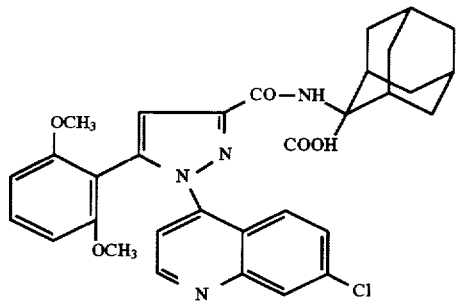

as the active ingredient, polyethylene glycol, NaOH, and water, wherein the mole equivalents of NaOH per mole equivalent of active ingredient is at least about 1.1, is suitable for soft gelatin capsule filling.

3 Claims, No Drawings

PHARMACEUTICAL FORMULATION

BACKGROUND OF THE INVENTION

SR48692 has shown considerable promise as an NT-antagonist for the treatment of psychosis. SR48692 and a method for the preparation thereof are described by Boigegrain et al in U.S. Pat. No. 5,420,141 (Example 186). SR48692 has the structural formula:

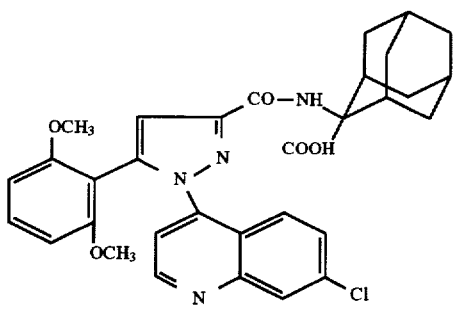

SR48692 has proven to be unusually difficult to formulate into pharmaceutical compositions, due in part to its very low solubility, even in organic solvents.

PCT/US87/02629 discloses a solvent system for enhancing the solubility of an acidic, basic or amphoteric pharmaceutical agent to produce a concentrated solution suitable for soft gelatin capsule filling. The solvent system comprises polyethylene glycol containing 0.2–1.0 mole equivalents of an ionizing agent per mole equivalent of pharmaceutical agent and 1–20% water. Attempts to formulate SR48692 in such a solvent system were not successful.

SUMMARY OF THE INVENTION

We have discovered a solvent system for SR48692 which produces a concentrated solution of the active ingredient suitable for soft gelatin capsule filling.

More specifically, in accordance with this invention, there is provided a pharmaceutical formulation comprising

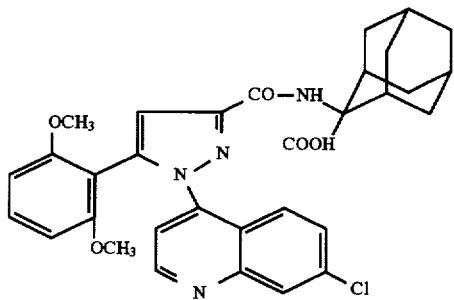

as the active ingredient, polyethylene glycol, NaOH, and $H_2O$, wherein the mole equivalents of NaOH per mole equivalent of agent is at least about 1.1.

DETAILED DESCRIPTION OF THE INVENTION

The polyethylene glycol used herein has an average molecular weight of between about 200–100,000 daltons (hereinafter, all molecular weights are expressed in daltons). Moreover, the molecular weight of polyethylene glycol selected affects the type of solution produced. Polyethylene glycol having an average molecular weight from about 200–800, preferably from about 300–700, and most preferably about 400, produces a soft gelatin capsule fill solution that is a liquid. Polyethylene glycol having an average molecular weight from about 800–10,000, preferably from about 2,000–8,000, produces a soft gelatin capsule fill solution that is semisolid, and polyethylene glycol having an average molecular weight between about 10,000–100,000, preferably about 15,000–60,000, produces a soft gelatin capsule fill solution that is solid.

Contemplated equivalents of polyethylene glycol include analogs, such as the polyethylene glycol ethers of various alcohols including but not limited to tetraglycol—the polyethylene glycol ether of tetrahydrofurfuryl alcohol, and copolymers of polyethylene glycol.

The polyethylene glycol can be present in amounts of 60–99%, preferably 70–98% and more preferably 80–95% by weight based on the total weight of the formulation.

The formulation can comprise 0.1–25%, preferably 0.5–20% and more preferably 1–15% by weight water.

The SR48692 can be present in an amount up to 10%, preferably 0.1–9% and more preferably 0.5–7.5% by weight.

The mole equivalents of NaOH present per mole of SR 48692 is at least about 1.1, preferably at least 1.2 and more preferably at least 1.3. Inadequate solubility of the agent was found at mole equivalents of 1.0 and less. Further, it was demonstrated that the NaOH could not be satisfactorily replaced by KOH.

The formulations of this invention can be prepared by adding aqueous NaOH to the polyethylene glycol. The active ingredient SR48692 is added to the PEG-NaOH until a solution is formed. Alternatively, the active ingredient can be dispersed in the PEG with mixing. Thereafter, the NaOH solution can be added resulting in dissolution of the active ingredient. Thereafter, the solution formulations can be encapsulated in a soft gelatin capsule according to techniques known in the art in order to form a pharmaceutical dosage form.

The following examples further illustrate the invention.

EXAMPLE 1

A 2.02 kg quantity of a 0.5% w/v sodium hydroxide solution was added to 20.4 kg of Polyethylene Glycol 400; this mixture was stirred until a clear solution was formed. To the polyethylene glycol 400/sodium hydroxide solution was added 100 g of SR48692; this mixture was stirred until the drug was completely dissolved by visual inspection. The resulting SR48692 solution was shipped to R. P. Scherer for encapsulation into soft gelatin capsules.

EXAMPLE 2

A 1.98 kg quantity of a 2.5% sodium hydroxide solution was added to 20.0 kg of Polyethylene Glycol 400; this mixture was stirred until a clear solution was formed. To the polyethylene glycol 400/sodium hydroxide solution was added 600 g of SR48692; this mixture was stirred until the drug was completely dissolved by visual inspection. The resulting SR48692 solution was shipped to R. P. Scherer for encapsulation into soft gelatin capsules.

EXAMPLE 3

A 1.92 kg quantity of a 6.0% w/v sodium hydroxide solution was added to 19.4 kg of Polyethylene Glycol 400; this mixture was stirred until a clear solution was formed. To the polyethylene glycol 400/sodium hydroxide solution was added 1.50 kg of SR48692; this mixture was stirred until the drug was completely dissolved by visual inspection. The resulting SR48692 solution was shipped to R. P. Scherer for encapsulation into soft gelatin capsules.

| Ingredient | Composition mg/capsule |
|---|---|
| SR48692 CAPSULE SOFT GELATIN 5 MG | |
| Polyethylene Glycol 400 | 1020 |
| Sodium Hydroxide | 0.500 |
| Purified Water | 100 |
| SR48692 | 5 |
| Soft Gelatin Capsule, White Opaque R. P. Scherer Capsule 18 Oblong (Die Size W18BD) Gel Formula 005LSMH Color 911 P | 1. Each |
| SR48692 CAPSULE SOFT GELATIN 30 MG | |
| Polyethylene Glycol 400 | 1000 |
| Sodium Hydroxide | 2.50 |
| Purified Water | 96.4 |
| SR48692 | 30 |
| Soft Gelatin Capsule, White Opaque R. P. Scherer Capsule 18 Oblong (Die Size W18BD) Gel Formula 005LSMH Color 911 P | 1. Each |
| SR48692 CAPSULE SOFT GELATIN 75 MG | |
| Polyethylene Glycol 400 | 969 |
| Sodium Hydroxide | 5.77 |
| Purified Water | 90.4 |
| SR48692 | 75 |
| Soft Gelatin Capsule, White Opaque R. P. Scherer Capsule 18 Oblong (Die Size W18BD) Gel Formula 005LSMH Color 911 P | 1. Each |

Having described the invention with reference to its preferred embodiments, it is to be understood that modifications within the scope of the invention will be apparent to those skilled in the art.

We claim:

1. A pharmaceutical formulation comprising from about 0.1 to about 10% w/v of the compound

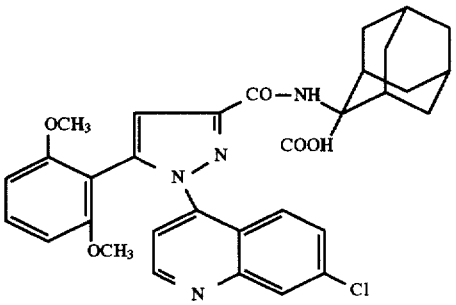

as the active ingredient,
polyethylene glycol,
NaOH, and
water, wherein the mole equivalents of NaOH per mole equivalent of active ingredient is at least 1.1.

2. The formulation of claim 1 wherein the ratio of mole equivalents of NaOH per mole equivalent of active ingredient is at least 1.2.

3. The formulation of claim 1 wherein the polyethylene glycol has a molecular weight of from 200–800.

\* \* \* \* \*